United States Patent

Orkin et al.

[11] Patent Number: 5,289,827
[45] Date of Patent: Mar. 1, 1994

[54] UTERINE CONTRACTION SENSING METHOD

[76] Inventors: Fredric L. Orkin, 672 Mallard La., Deerfield, Ill. 60015; Robert Czarnek, 616 Fairview Ave., Blacksburg, Va. 24060

[21] Appl. No.: 852,557
[22] Filed: Mar. 17, 1992
[51] Int. Cl.⁵ .............................................. A61B 5/103
[52] U.S. Cl. .................................. 128/775; 128/778; 128/782
[58] Field of Search ............... 128/774, 775, 778, 782, 128/721; 338/254, 275, 204, 47, 99, 197, 199

[56] References Cited

U.S. PATENT DOCUMENTS

| | | |
|---|---|---|
| Re. 31,158 | 2/1983 | Carter et al. . |
| 3,806,471 | 4/1974 | Mitchell ............... 338/99 |
| 3,913,563 | 10/1975 | Ball . |
| 4,268,815 | 5/1981 | Eventoff et al. . |
| 4,276,538 | 6/1981 | Eventoff et al. . |
| 4,301,337 | 11/1981 | Eventoff . |
| 4,314,227 | 2/1982 | Eventoff . |
| 4,314,228 | 2/1982 | Eventoff . |
| 4,315,238 | 2/1982 | Eventoff . |
| 4,426,884 | 1/1984 | Polchaninoff . |
| 4,451,714 | 5/1984 | Eventoff . |
| 4,489,302 | 12/1984 | Eventoff . |
| 4,503,705 | 3/1985 | Polchaninoff . |
| 4,509,527 | 4/1985 | Fraden . |
| 4,570,150 | 2/1986 | Zandman et al. ............... 338/329 |
| 4,630,613 | 12/1986 | Dennis . |
| 4,734,034 | 3/1988 | Maness et al. . |
| 4,738,268 | 4/1988 | Kipnis . |
| 4,739,299 | 4/1988 | Eventoff et al. . |
| 4,781,200 | 11/1988 | Baker . |
| 4,785,822 | 11/1988 | Wallace . |
| 4,793,193 | 12/1988 | Borgudd ............... 73/862.04 |
| 4,810,922 | 3/1989 | Hirsch . |
| 4,856,993 | 8/1989 | Maness et al. . |
| 4,860,768 | 8/1989 | Hon et al. . |
| 4,873,986 | 10/1989 | Wallace . |
| 4,873,990 | 10/1989 | Holmes et al. . |
| 4,898,179 | 2/1990 | Sirota ............... 128/670 |
| 4,909,263 | 3/1990 | Norris . |
| 4,913,162 | 4/1990 | Leang et al. ............... 128/774 |
| 4,942,882 | 7/1990 | Bellinson . |
| 4,944,307 | 7/1990 | Hon et al. . |
| 4,947,853 | 8/1990 | Hon . |
| 4,947,865 | 8/1990 | Hon et al. . |
| 4,949,730 | 8/1990 | Cobben et al. . |
| 4,953,563 | 9/1990 | Kaiser et al. . |
| 4,966,152 | 10/1990 | Gäng et al. . |
| 4,966,161 | 10/1990 | Wallace et al. . |
| 4,967,761 | 11/1990 | Nathanielsz . |
| 4,989,615 | 2/1991 | Hochberg . |
| 5,012,817 | 5/1991 | Zeilinski et al. ............... 128/744 |
| 5,025,787 | 6/1991 | Sutherland et al. . |
| 5,033,291 | 7/1991 | Podoloff et al. . |
| 5,053,585 | 10/1991 | Yaniger . |
| 5,086,785 | 2/1992 | Gentile et al. ............... 128/782 |

OTHER PUBLICATIONS

Interlink Electronics Product Specification, Feb. 1991, author unknown, 16 pages.

Primary Examiner—Stephen C. Pellegrino
Assistant Examiner—Guy V. Tucker
Attorney, Agent, or Firm—Webb, Burden, Ziesenheim & Webb

[57] ABSTRACT

An extra-uterine sensing device for directly measuring changes in pressure brought about by uterine contractions of a wearer. The sensing device includes an outer member adapted for fixed attachment to the abdomen in an area of the wearer's uterus to establish a minimum pre-load and a sensor unit positioned between the outer member of the abdomen. The sensor unit includes a variable resistor formed of a pressure sensitive ink, a first electrically conductive member interfacing with the ink and a second electrically conductive member interfacing with the ink and spaced from the first electrically conductive member and a device attached to the first and second electrically conductive members to monitor changes in the electrical resistance. Also disclosed is an extra-uterine method of sensing uterine contractions of a wearer having a fundus including attaching a sensing device of the type described to the abdomen in the area of the wearer's uterus creating a minimum pre-load on the sensing device sufficient to establish the reference level for instantaneously detecting changes in pressure caused by contractions, non-mechanically and directly converting a change in pressure to a change in electrical resistance and converting the change in resistance to a non-decaying electrical signal and monitoring the electrical signal.

1 Claim, 4 Drawing Sheets

UTERINE CONTRACTION SENSING METHOD

BACKGROUND OF THE INVENTION

1. Field of the Invention

This invention relates generally to fetal monitoring apparatuses and, more particularly, to an apparatus for sensoring uterine activity, in particular, contractions.

2. Description of the Prior Art

Fetal monitors, which are typically quite sophisticated, are widely used to monitor the uterine activity of pregnant women, as well as the condition of the fetus and the uterus. Analysis of uterine contractions, in conjunction with fetal heart rate, during the pregnancy and labor yields significant information concerning the condition of the fetus as well as the advancement of labor. Such monitoring is particularly helpful in so-called difficult pregnancies to systematically evaluate fetal stress, but it is certainly of use in more routine pregnancies as well.

Information of fetal distress will result in prompt remedial action, including a cesarean delivery, both during pregnancy and/or during actual labor. Likewise, early contractions can be treated so as to achieve full-term pregnancies. Examples of currently available fetal monitors include the FetaScan from International Biomedics, Inc., the Corometrics 115 and the Hewlett-Packard 8040A.

Such fetal monitors, however, regardless of their sophistication, require a device or element to actually sense the uterine contractions.

These elements can be intra-uterine or extra-uterine. An example of an intra-uterine sensing element is a catheter which is capable of measuring uterine activity within the uterine cavity itself. Such sensors are disclosed in U.S. Pat. Nos. 4,785,822; 4,873,986; 4,873,990; 4,909,263; 4,942,882; 4,944,307; 4,953,563 and 4,966,161. However, these devices are invasive. Further, they cannot be used for pre-term monitoring because they are invasive.

Other devices, known as tocotonometers, are capable of non-invasively sensing uterine activity and therefore are widely used with fetal monitors. Tocotonometers measure the hardness of the abdomen wall, which is an indication of the uterine activity, by various mechanical means. Specifically, tocotonometers include strain gauge elements mounted to an elastic beam. Tocotonometers are expensive, structurally delicate, i.e., break easily, and are difficult to sanitize between uses. In use, the tocotonometer is held adjacent to the abdomen, usually by a belt-like device, in the vicinity of the fundus, i.e., the top of the uterus. The tocotonometer after pre-load by the belt responds with a constant recording level between contractions. The output of the tocotonometer is transmitted to the fetal monitor. Examples of such tocotonometers are manufactured by Huntleigh, Model #447, Corometrics, Model #2260 and Hewlett-Packard, Model #15248A. Other types of mechanical-type sensors for measuring uterine contractions are disclosed in U.S. Pat. Nos. 3,913,563; 4,949,730; 4,966,152 and 4,989,615. Like the tocotonometers, these devices are expensive, complicated in construction and use and difficult to sanitize between uses. The sensor disclosed in U.S. Pat. No. 4,949,730 utilizes a piezoelectric element which cannot measure contractions over a sustained period of time because the charge of the piezoelectric element dissipates quickly, say on the order of several seconds.

Accordingly, it is an object of the present invention to provide an apparatus and method for detecting uterine activity which is inexpensive, non-complicated in construction and easy to operate.

It is a further object of the present invention to provide an apparatus for detecting uterine activity which can be easily cleaned.

It is a further object of the present invention to provide an apparatus for detecting uterine activity which can be made disposable or reusable as required.

It is a further object of the present invention to provide an apparatus with a signal for detecting uterine activity which does not decay over time.

It is yet a further object of the present invention to provide an apparatus for detecting uterine activity which can be interchangeable with presently available fetal monitors.

SUMMARY OF THE INVENTION

Our invention is an extra-uterine sensing device for directly measuring changes in pressure brought about by uterine contractions of a wearer and includes an outer member adapted for fixed attachment to the abdomen in an area of a wearer's uterus and fundus to establish a minimum pre-load, and a sensor unit positioned between the outer member and the abdomen. The sensor unit includes a variable resistor formed of a pressure sensitive ink, a first electrically conductive member interfacing the ink, and a second electrically conductive member interfacing the ink and spaced from the first electrically conductive member. A device attaches to the first and second electrically conductive members to monitor changes in the electrical resistance.

The variable resistor, the first electrically conductive member and the second electrically conductive member are sandwiched between a first sheet and a second sheet, wherein the outer member comprises the first sheet. The first sheet attaches to the second sheet sealing the first electrically conductive member, the second electrically conductive member and the variable resistor. The first sheet can be rigid and made of a polymeric material, or can be a metal having a coating made of an electrical insulator. The second sheet can be flexible.

The extra-uterine sensing device can further include a belt that receives the outer member, the belt being capable of establishing a minimum pre-load. Alternatively, a weight can be adapted to rest on the outer member where the weight is capable of establishing the minimum pre-load. The sensor can be made in such a manner that it is disposable.

The variable resistor can be sandwiched between the first electrically conductive member and the second electrically conductive member. In this manner preferably, the variable resistor is deposited on the first electrically conductive member. Alternatively, the variable resistor is defined by a first layer deposited on the first electrically conductive member and a second layer deposited on the second electrically conductive member. The variable resistor can have two sides where the first electrically conductive member and the second electrically conductive member contact the variable resistor on the same side.

Preferably, the first electrically conductive member has a first base and a plurality of first legs depending therefrom, where the first legs define first receiving spaces therebetween. The second electrically conductive member also has a second base and a plurality of second legs depending therefrom, where the second legs define second receiving spaces therebetween. The first base and the first legs are spaced from the second base and the second legs so that the first legs are received by the second receiving spaces and the second legs are received by the first receiving spaces. Preferably, the variable resistor has a substantially linear pressure to conductance relationship over a range of 0–100 mm mercury.

The extra-uterine sensing device can further include at least one non-pressure sensitive resistor electrically coupled to one of the electrically conductive members with the non-pressure sensitive resistor being formed of a non-pressure sensitive resistive ink. It is preferable that the value of the variable resistor and the non-pressure sensitive resistor are calibrated to predetermined values.

Our invention also includes an extra-uterine method of sensing uterine contractions of a wearer that includes attaching the sensor device to the abdomen in the area of the wearer's uterus. This sensor includes a variable resistor formed of pressure sensitive ink, a first electrically conductive member interfacing with the ink and a second electrically conductive member interfacing with the ink and spaced from the first electrically conductive member. A minimum pre-load is created on the sensing device sufficient to establish a reference level for instantaneously detecting changes in the pressure caused by contractions. The changes in pressure are then non-mechanically and directly converted to a change in electrical resistance and the change in resistance is then converted to a non-decaying electrical signal which is monitored.

The sensor can be formed by printing the variable resistor using the pressure sensitive ink and interfacing the first electrically conductive member and the second electrically conductive member with the variable resistor. The sensor can further be formed by printing the first electrically conductive member and the second electrically conductive member using electrically conductive ink. The method can further include electrically coupling a non-pressure sensitive resistor to one of the electrically conductive members where the non-pressure sensitive resistor is formed of resistive ink. The method can further include calibrating the sensor in a fixed load condition, such as by removing a portion of the non-pressure sensitive resistors.

DESCRIPTION OF THE PREFERRED EMBODIMENTS

Figure 1:
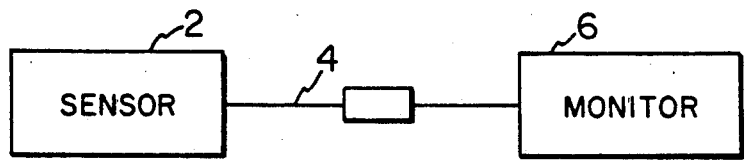
FIG. 1 shows a schematic of an extra-uterine sensor connected to a monitor.

FIG. 1 shows a schematic of an extra-uterine contraction monitoring system in general. The system includes a sensor 2 that rests against the abdomen of a wearer. Electrical leads 4 attach to the sensor and connect to a monitor 6. An electrical signal is generated as a function of uterine contractions and the electrical signal passes from the sensor 2 along the leads 4 to the monitor 6 which interprets the data or displays the data for medical personnel to interpret.

Figure 2:
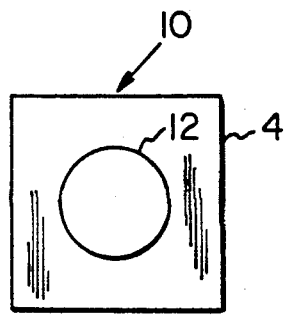
FIG. 2 shows a prior art extra-uterine sensor.
Figure 3:
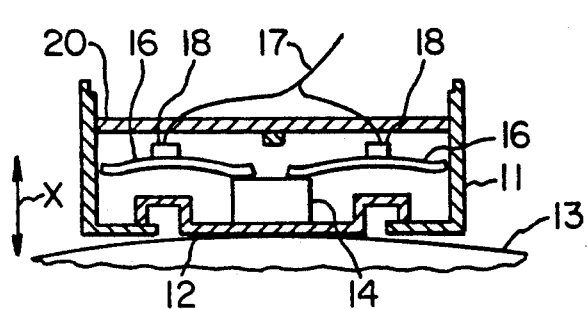
FIG. 3 is a side view, partially in section, of the sensor shown in FIG. 2.

FIGS. 2 and 3 show a prior art extra-uterine contraction sensor 10 of the type manufactured by Huntleigh, Model #447. The sensor 10 includes a base 11 having a centrally positioned flexible member 12 made of rubber. The outer surface of flexible member 12 is adapted to rest on the abdomen of a wearer 13 having uterine contractions near the fundus area. A button 14 rests on an inner surface of the flexible member 12. Curved spring steel members 16 abut or are attached to an upper end of the button 14. A plurality of strain gauges 18 attach to the curved spring steel member 16. The strain gauges 18 are electrically connected to each other by leads 17 to form a Wheatstone bridge. A stop member 20 is positioned above the button 14 limiting displacement in the axial direction X of the button 14.

In use, the sensor is placed on the abdomen of a wearer having uterine contractions. A voltage potential is placed across the Wheatstone bridge. Each contraction causes axial displacement of the flexible member 12, the button 14 and spring steel members 16 relative to the base 11. This causes a change in resistance to the strain gauges, changing the balance of the Wheatstone bridge. The Wheatstone bridge in turn produces an electrical signal that correlates to the strength of the uterine contractions and is measured by the monitor 6.

Figure 4:
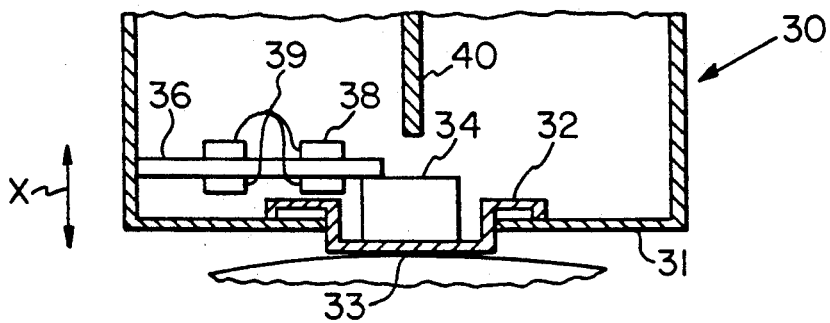
FIG. 4 is a cross section, partially in section, of another extra-uterine sensor.

FIG. 4 shows another prior art extra-uterine contraction sensor 30 of the type manufactured by Corometrics, Model #2260. Sensor 30 includes a base 31 having a centrally positioned flexible member 32 made of rubber. The outer surface of the flexible member 32 is adapted to rest on the abdomen and near the fundus of a wearer 33 having uterine contractions. A button 34 is positioned on an inner surface flexible member 32. A cantilever beam 36, made typically of spring steel, rests on an upper surface of the button 34. A plurality of strain gauges 38, typically four, electrically connect to each other by leads 39 forming a Wheatstone bridge. A stop member 40 is positioned above the beam 36 limiting the displacement in the axial direction X of the button 34 and the beams relative to the base 31. Sensor 30 operates similarly in the same manner as sensor 10 where displacement of the cantilever beam 36 causes a resistance change of the Wheatstone bridge which correlates to uterine contractions.

Figure 5:
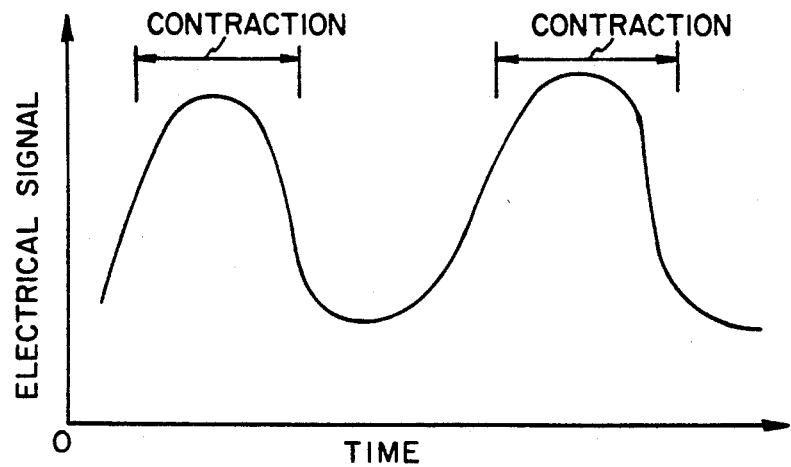
FIG. 5 is a showing the relationship of time versus electrical signal of a sensor measuring uterine contractions.
Figure 6:
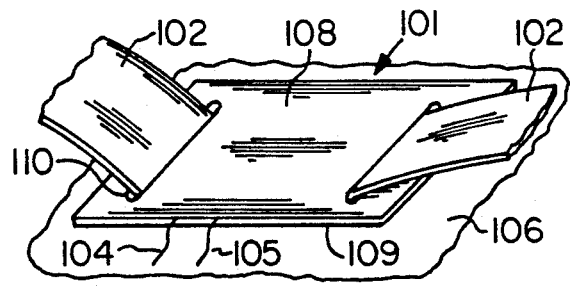
FIG. 6 is a top partial perspective view of the sensor made in accordance with the present invention.
Figure 7:
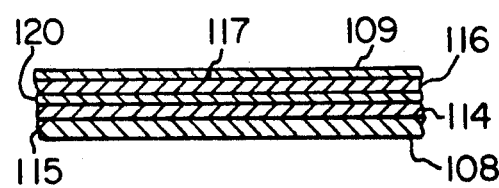
FIG. 7 is a side view, partially in section, of the sensor shown in FIG. 6.
Figure 8:
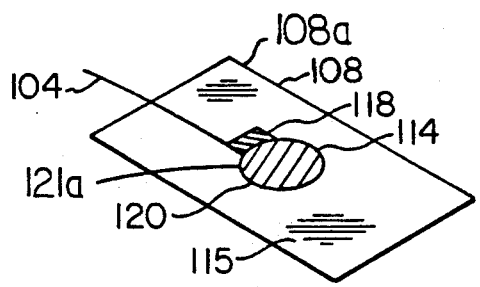
FIG. 8 is a top perspective view of a portion of the sensor shown in FIG. 6.
Figure 9:
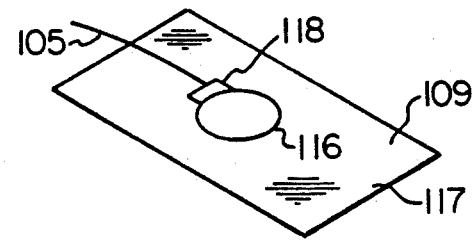
FIG. 9 is a top perspective view of a portion of the sensor shown in FIG. 6.

FIG. 5 shows a typical signal relationship of the change in the electrical signal produced by the Wheatstone bridge as a function of time when either sensor 10 or 30 measures uterine contractions. As discussed previously, these prior art sensors are expensive, mechanically sensitive and difficult to clean. Applicants' invention as discussed below overcomes these problems.

FIGS. 6 through 12 show a first embodiment of an extra-uterine sensing device 100 made in accordance with the present invention and which includes a sensor 101. A belt 102 attaches the sensor 101 to the wearer. Electrical lead wires 104, 105 electrically couple the sensor 101 to the monitor 6 previously discussed. The belt 102 maintains the sensor 101 in a pre-load or threshold condition on the abdomen and near the fundus of the wearer 106 having uterine contractions.

The sensor 101 includes a backing member or back sheet 108 attached to a front sheet 109. The rigid back sheet 108 includes a perimeter 108a. Preferably, the back sheet 108 is made of a rigid material and the front sheet 109 is made of a flexible material. The back sheet 108 can be made from either a polymeric material, such as plastic formed of a quarter inch of ribbed plastic material, or a metal having an electrically insulated coating. The front sheet can be made from a thin plastic foil, for example, 0.005" Lexan ® film manufactured by General Electric Corporation. The backing member 108 has two slots 110 through which opposite ends of the belt 102 connect. Alternatively, the backing member 108 can have four slots.

A first electrical conductive member or electrode 114 attaches to an inner surface 115 of backing member 108 and a second electrically conductive member 116 attaches to an inner surface 117 of front sheet 109. The conductive members 114 and 116 can be formed from an electrically conductive ink, such as Chromerics 4407, 4408 or 440X, and deposited on respective sheets 108 and 109. Alternatively, the conductive members 114 and 116 can be metal conductors attached to or embedded in the surface, such as printed circuit boards or over-molded metal contacts. First ends of the electrically conductive members 114 and 116 terminate at an electrical connector 118 that electrically couples conductive members 114 and 116 to respective lead wires 104, 105.

Figure 10:
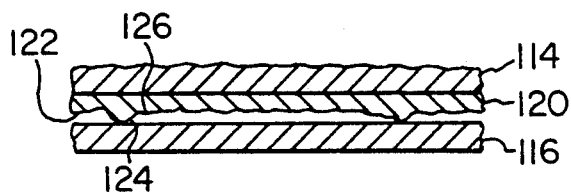
FIG. 10 is a side view, partially in section, of a portion of the sensor shown in FIG. 6.
Figure 11:
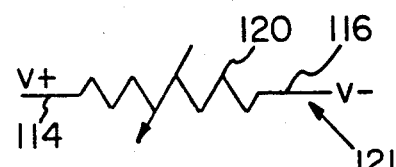
FIG. 11 is a schematic of an electric circuit of the sensor shown in FIG. 6.

A pressure sensitive ink is deposited on conductive member 114 forming a variable resistor 120. Pressure sensitive resistive inks are known in the art, for example, Chromerics, Inc., a Grace company, manufactures a CHO-FLEX 440X family of pressure sensitive inks. Pressure sensitive inks also are described in U.S. Pat. Nos. 5,033,291; 4,734,034 and 4,856,993. The variable resistor 120 has a rough outer surface 122 comprised of a plurality of hills and valleys 124 and 126, respectively, as shown in FIG. 10, which is an enlarged view of a portion of the sensor 101. The second electrically conductive member 116 rests on the rough surface 122 so that conductive members 114 and 116 sandwich the variable resistor 120 forming a circuit or sensing unit 121 as schematically shown in FIG. 11. The circuit or sensing unit 121 includes a perimeter 121a. The perimeter 121a of the circuit or sensing unit 121 is contained within the perimeter 108a of the rigid back sheet 108.

Figure 12A:
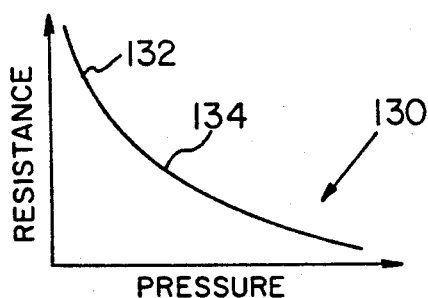
FIG. 12A is a pressure versus resistance curve of the variable resistor of the sensor shown in FIG. 6.
Figure 12C:
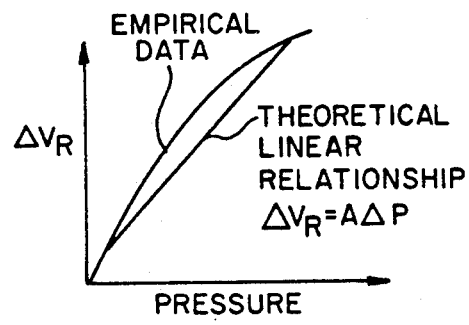
FIG. 12C is a schematic showing the change in voltage with respect to the pressure of the circuit shown in FIG. 12B.
Figure 12B:
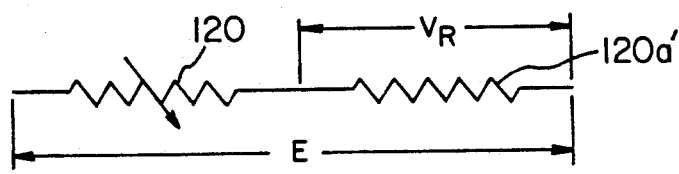
FIG. 12B is a circuit of a sensor similar to that shown in FIG. 6.

The resistance of the interface between the conductive member and the above-described inks or between two separate layers of the above-described inks decreases with an increase in pressure as shown in FIG. 12A. This is believed to be caused by a flattening of the surface 122 and improving the contact surface area of conductive member 116 with variable resistor 120. As shown in FIG. 12A, the curve 130 has a linear portion 132 and a non-linear portion 134. Alternatively, a resistor of relatively low value compared to the variable resistor 120 may be connected in series to the variable resistor 120, as shown in FIG. 12B. FIG. 12C shows the relationship between resistance of the sensor and the applied pressure when the variable resistor 120 is connected with a small resistor 120a' and excitation voltage E (approximately 5 volts) is applied as shown in FIG. 12B. Specifically, in theory, a change in the variable resistor 120 can be measured in terms of a change in voltage drop $\Delta V_R$ across resistor 120a' since the current through both resistors is always the same (Ohm's law).

Empirical data taken by the inventors of the voltage drop, $\Delta V_R$, and the pressure is also shown in FIG. 12C.

In the range of pressure P associated with uterine contractions (between a pressure of 0 mm–100 mm Hg), a substantially linear relationship can be approximated by the equation:

$$\Delta V_R = A \times \Delta P$$

where A is a constant.

The sensor 101 can be manufactured through automated technology whereby the various inks are deposited on the respective sheets 108 and 109 and then the sheets 108 and 109 are attached to each other. Accordingly, the sensor 101 can be made for a fraction of the cost of the prior art tocotonometers, which require complicated mechanisms and strain gauge circuits. Thus, the sensor 101 can be disposable because of this low cost. Alternatively, the sensor can be sealed about its edges 150 so that it can easily be disinfected or sanitized and reused. Furthermore, since the sensor 101 has no moving mechanical parts, such as the spring members and the buttons used in the prior art tocotonometers, the possibility of damage by environmental vibration or shocks to the sensor 101 is minimized.

The geometries of the conductive members 114 and 116 can vary from simple circles and rectangles to more complicated shapes, such as intersecting forks and spirals. One manufacturer of such arrangements is Interlink Electronics, Incorporated, Carpinteria, Calif.

Figure 13:
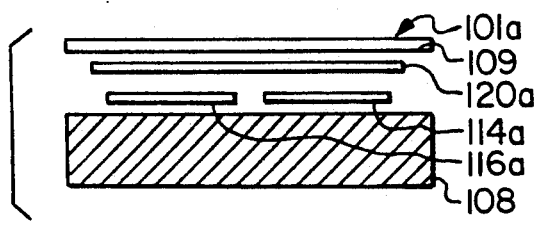
FIG. 13 is an exploded side view, partially in section, of another embodiment of an extra-uterine sensor made in accordance with the present invention.
Figure 15:
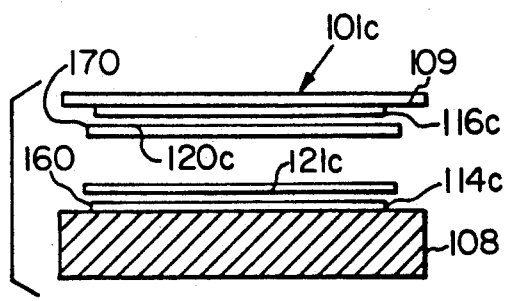
FIG. 15 is an exploded view, partially in section, of another embodiment of an extra-uterine sensor made in accordance with the present invention.
Figure 14:
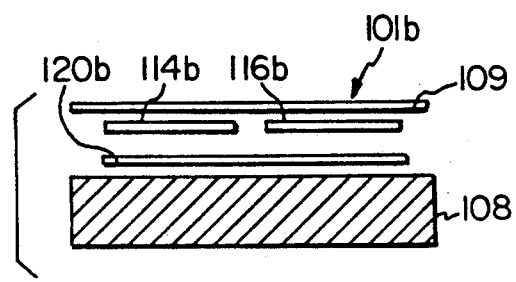
FIG. 14 is an exploded view, partially in section, of another embodiment of an extra-uterine sensor made in accordance with the present invention.

FIGS. 13, 14 and 15 show various geometric modifications of the conductive members 114 and 116 and resistive member 120. Like parts have like reference numerals. Specifically, FIG. 13 shows a sensor 101a having a variable resistor 120a made of the pressure sensitive ink deposited on an inner surface of sheet 109. Two spaced-apart conductive members 114a, 116a made of conductive ink are deposited on an inner surface of sheet 108.

FIG. 14 shows a sensor 101b having a variable resistor 120b made of the pressure sensitive ink deposited on an inner surface of sheet 108. Two spaced-apart conductive members 114b, 116b made of conductive ink are deposited on an inner surface of sheet 109.

FIG. 15 shows a sensor 101c having spaced-apart conductive members 114c, 116c deposited on respective inner surfaces of sheets 108, 109. Variable resistive pressure sensitive ink is then deposited on surfaces 160, 170 of conductive members 114c, 116c, respectively, forming variable resistors 120c, 121c so that the resistance of the interface between resistors 120c and 121c decreases with an increase in pressure. Resistor 120c rests on resistor 121c. The embodiments shown in FIGS. 13–15 are preferable to the sensor 101 because these sensors minimize or eliminate the possibility of an electrical short caused by a scratch on the resistor to cause conductive members 114, 116 to directly contact each other.

Figure 16:
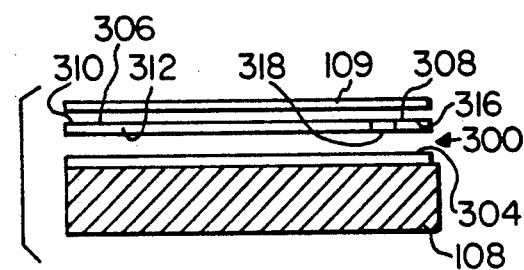
FIG. 16 is an exploded view, partially in section, of yet another embodiment of an extra-uterine sensor made in accordance with the present invention.
Figure 17:
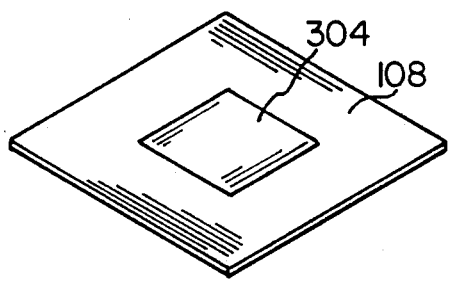
FIG. 17 is a top perspective view of a portion of the sensor shown in FIG. 16.
Figure 18:
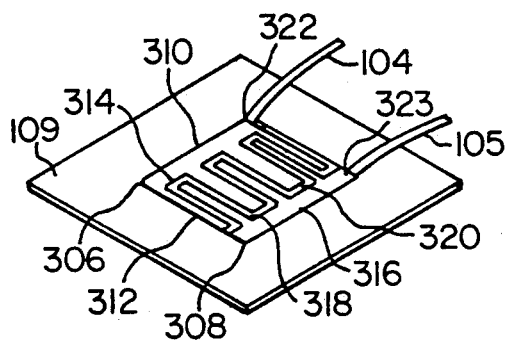
FIG. 18 is a top perspective view of a portion of the sensor shown in FIG. 16.

FIGS. 16–18 show yet another embodiment of a sensor 300 of the present invention and is similar to the embodiment shown in FIG. 13 except that the conductive members are made from fork-like members; and, thus, like reference numerals are used for like parts. Sensor 300 includes a back sheet 108 having a variable pressure sensitive resistive member 304 made of resistive ink deposited thereon. A front sheet 109 has two spaced-apart conductive members 306, 308 made of electrically conductive ink deposited on an inner surface of sheet 109. The first electrically conductive member 306 includes a base 310 having a plurality of legs 312 depending therefrom. Spaces 314 are defined by the legs 312 and base 310. Likewise, the second electrically conductive member 308 includes a base 316 having a plurality of legs 318 depending therefrom. Spaces 320 are defined by the legs 318 and base 316. Respective spaces 314 and 320 accommodate legs 318 and 312. Respective ends 322, 323 of members 306, 308 attach to lead wires 104, 105 that connect to the monitor 6.

Figure 19:
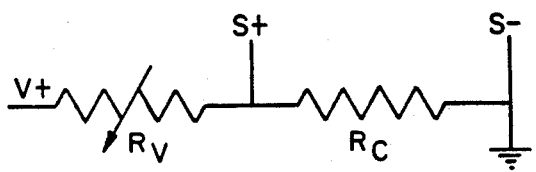
FIG. 19 is a schematic showing the electrical circuit of the sensor shown in FIG. 16.

Preferably, as shown in FIG. 19, a non-pressure sensitive resistor $R_c$ is electrically coupled in series with the pressure sensitive resistor $R_v$ formed by resistive member 304 and conductive members 306 and 308 so that a highly sensitive sensor can be provided without the need for a Wheatstone bridge. Preferably, the resistor is either a potentiometer or a trimmable resistor made of a non-pressure sensitive resistive ink, such as Chromerics 4430, 4432.

Figure 20:
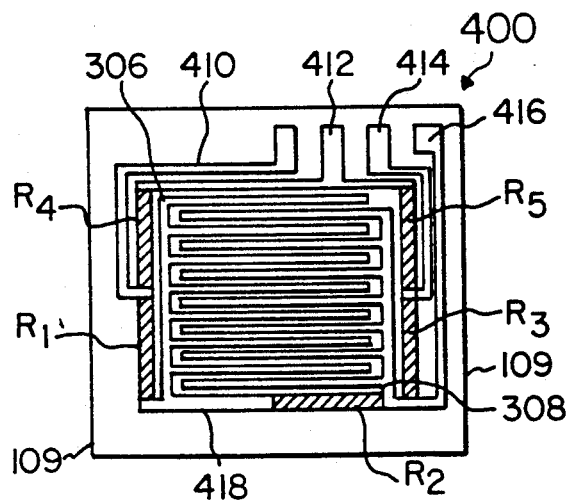
FIG. 20 is a portion of another embodiment of an extra-uterine sensor made in accordance with the present invention.
Figure 21:
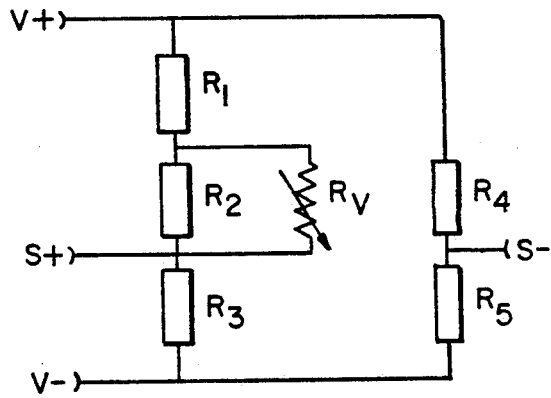
FIG. 21 is a schematic of an electrical circuit of the embodiment shown in FIG. 20.

FIG. 20 shows a sensor 400 similar to sensor 300 shown in FIGS. 16–18, and accordingly like reference numerals will be used to describe like parts. The only difference between the sensors is the arrangement of conductive members 306 and 308 on sheet 109. Sensor 400 includes non-pressure sensitive resistors $R_1$, $R_2$, $R_3$, $R_4$ and $R_5$ and electrically conductive segments 410, 412, 414, 416 and 418 electrically coupled as shown in FIG. 21. $R_v$ is formed by resistive member 304. The resistors are related as follows:

$$(R_1 + R_2)/R_3 = \frac{R_4}{R_5}$$

The resultant electrical circuit forms a Wheatstone bridge. The output voltages S+, S− can be conditioned by choosing appropriate resistor values so that the impedance and output of the circuit match that of the sensors. Therefore, sensor 400 can be used as a replacement for prior art sensors with existing monitors 6. Preferably, the conductive segments 410, 412, 414, 416 and 418 are formed from the same conductive ink as conductive members 306 and 308 and the resistors $R_1$, $R_2$, $R_3$, $R_4$ and $R_5$ are formed of a resistive ink which does not change resistant values as a function of pressure. Thus, the above-described resistors and conductors can easily and inexpensively be printed on sheet 109. The resistors $R_1$, $R_2$, $R_3$, $R_4$ and $R_5$ can then be trimmed, i.e., modified after they are printed onto the circuit by removing some of the resistive ink so that the voltage of the circuit shown in FIG. 21 across S+ and S− is a predetermined value, so that the resistors can be calibrated for a fixed load or pressure resulting in a specific sensitivity of the sensor.

Figure 22:
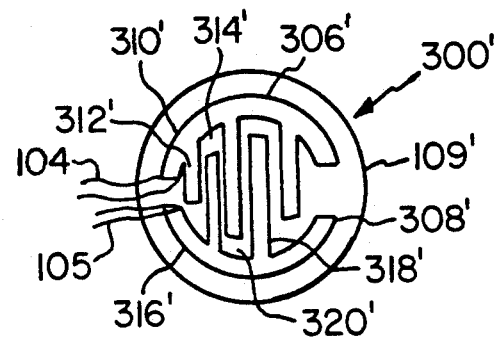
FIG. 22 is yet another embodiment of the extra-uterine sensor made in accordance with the present invention.

Actual prototypes were made incorporating both the electrical circuit shown in FIG. 19 and the circuit shown in FIG. 21 using a 1″ diameter Interlink Sensor Part No. E050, as shown in FIG. 22, which is similar to sensor 300 except that it is circular. Like primed part numbers are used for like parts. With respect to the circuit shown in FIG. 19:

$R_c = 5$ KΩ
$R_v = 1''$ diameter Interlink Sensor Part No. E050
$V+ = 5$ V

With respect to the circuit shown in FIG. 21:

$R_1 = 5$ KΩ
$R_2 = 5$ KΩ
$R_v = 1''$ Interlink Sensor Part No. E050
$R_3 = 5$ KΩ
$R_4 = 10$ KΩ
$R_5 = 5$ KΩ
$V- = 0$ V
$V+ = 5$ V.

Figure 23:
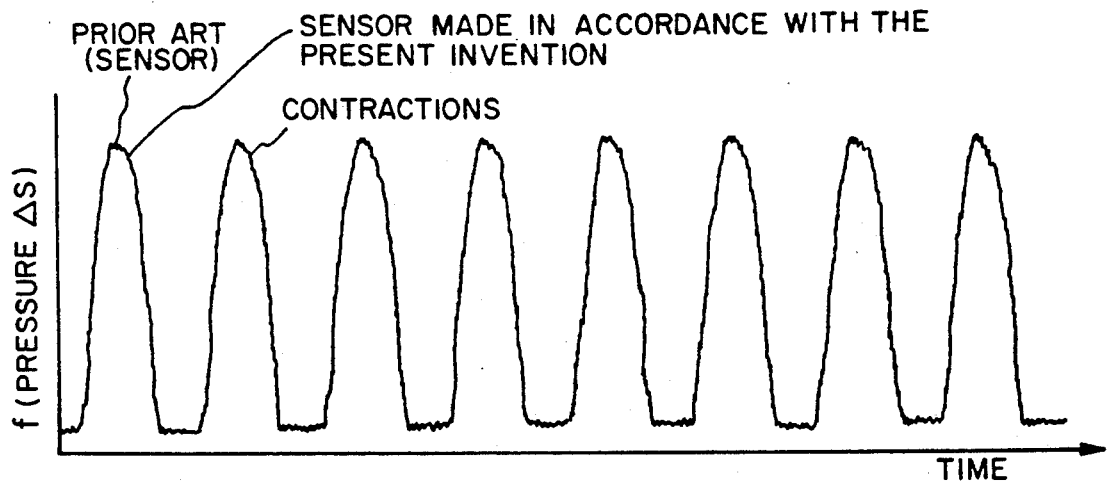
FIG. 23 shows a chart recorder reading comparing pressure readout as a function of time measuring uterine contractions comparing prior art sensors with a sensor made in accordance with the present invention.

FIG. 23 compares the voltage drop across S+ and S− as shown in FIG. 21 with the corresponding output voltage, a Huntleigh sensor, Model #447, over a range of simulated contractions having a maximum pressure of 100 mm Hg. As is evident, the voltage drop across S+ and S− and the voltage output of the Huntleigh sensor are almost identical; therefore, it is believed the sensors can be substituted for each other.

In all of the above devices, the sensor attaches to the abdomen in the area of the wearer's fundus. The belt is then tightened to create a minimum pre-load condition on the sensing device sufficient to establish a reference level for instantaneously detecting changes in the pressure caused by contractions. Alternatively, in all of the above-described devices, the belt can be replaced by a weight resting against the abdomen so that the sensor is placed in a pre-load condition to give a reference level so that all contractions are immediately sensed. In this arrangement, the sensors non-mechanically and directly convert the change in pressure to an electrical resistance. The change in resistance is converted to a non-decaying electrical signal and the electrical signal is monitored by the monitor 6 of FIG. 1.

Having described the presently preferred embodiments of our invention, it is to be understood that it may otherwise be embodied within the scope of the appended claims.

We claim:

1. An extra-uterine method of sensing uterine contractions of a wearer having a uterus utilizing a non-mechanical sensor which directly converts a change in pressure to a change in electrical signal, the method comprising:

A. attaching a sensor to the abdomen in the area of the wearer's uterus, said sensor including:

a rigid outer member, an inner member, and a sensing unit, said sensing unit positioned between said inner member and said rigid outer member, said sensing unit including:

i. a variable resistor having an outer surface and formed of a pressure sensitive ink; and ii. a first electrically conductive member interfacing with said ink, wherein said inner member rests on the abdomen;

B. creating a mechanical pre-load on the sensing unit and forcing the first electrically conductive member against the variable resistor outer surface, thereby creating a reference level electrical resistance;

C. creating a reference level non-decaying electrical signal corresponding to said reference level electrical resistance;

D. changing the force applied to the first electrically conductive member against the variable resistor outer surface in response to uterine contractions and instantaneously and non-mechanically changing the electrical resistance of the variable resistor, thereby non-mechanically and directly converting a change in pressure to a change in electrical resistance;

E. creating a non-decaying electrical signal corresponding to said changing electrical resistance; and F. monitoring uterine contractions by monitoring the electrical signal corresponding to said changing force.

* * * * *

UNITED STATES PATENT AND TRADEMARK OFFICE
CERTIFICATE OF CORRECTION

PATENT NO. : 5,289,827
DATED : March 1, 1994
INVENTOR(S) : Fredric L. Orkin and Robert Czarnek It is certified that error appears in the above-indentified patent and that said Letters Patent is hereby corrected as shown below:

Title page, after [76] Inventors:, "Fredric L. Orkin" should read
--Fredric L. Orkin--.

Column 3 Line 58 after "is a" insert --graph--.

Column 6 Line 24 after "108." insert --This results in a substantially rigid sensor 101.--.

Signed and Sealed this

Ninth Day of August, 1994

Attest:

BRUCE LEHMAN

*Attesting Officer*   *Commissioner of Patents and Trademarks*